US012629120B2

(12) United States Patent
Watanabe et al.

(10) Patent No.: US 12,629,120 B2
(45) Date of Patent: May 19, 2026

(54) MAMMOGRAPHY APPARATUS AND SAMPLE IMAGING ASSISTANCE SET

(71) Applicant: FUJIFILM CORPORATION, Tokyo (JP)

(72) Inventors: Hiroshi Watanabe, Kanagawa (JP); Shunsuke Nishimura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 150 days.

(21) Appl. No.: 18/815,949

(22) Filed: Aug. 27, 2024

(65) Prior Publication Data

US 2025/0072855 A1 Mar. 6, 2025

(30) Foreign Application Priority Data

Aug. 30, 2023 (JP) ................................. 2023-140485

(51) Int. Cl.
*A61B 6/00* (2024.01)
*A61B 6/04* (2006.01)
*A61B 6/50* (2024.01)

(52) U.S. Cl.
CPC ............ *A61B 6/502* (2013.01); *A61B 6/0414* (2013.01); *A61B 6/54* (2013.01)

(58) Field of Classification Search
CPC .......... A61B 6/0414; A61B 6/502; A61B 6/54
See application file for complete search history.

(56) References Cited

U.S. PATENT DOCUMENTS

2011/0021947 A1* 1/2011 Nakayama ............. A61B 6/469
378/37

FOREIGN PATENT DOCUMENTS

JP 2011-024748 A 2/2011

* cited by examiner

*Primary Examiner* — Dani Fox
(74) *Attorney, Agent, or Firm* — Studebaker Brackett PLLC

(57) ABSTRACT

A mammography apparatus including: an imaging table that has a placement surface on which a breast is placed; a protective cover that includes a first magnetic object at a predetermined first position and is mounted on the placement surface; and a sample tray that includes a second magnetic object and a housing part of a sample and is placed on the placement surface via the protective cover, the second magnetic object being attracted to the first magnetic object by a magnetic force, wherein the sample tray is configured to be magnetically attached to the predetermined first position of the protective cover by the first magnetic object and the second magnetic object.

14 Claims, 6 Drawing Sheets

MAMMOGRAPHY APPARATUS AND SAMPLE IMAGING ASSISTANCE SET

CROSS-REFERENCE TO RELATED APPLICATIONS

This application claims priority from Japanese Application No. 2023-140485, filed on Aug. 30, 2023, the entire disclosure of which is incorporated herein by reference.

BACKGROUND

Technical Field

The present disclosure relates to a mammography apparatus and a sample imaging assistance set.

Related Art

In the related art, a mammography apparatus including a biopsy unit for performing so-called biopsy for collecting a tissue of a site of a breast that is suspected of having a lesion and performing a precise examination has been developed. For example, JP2011-024748A discloses a method of performing radiography in a state where a breast disposed on an imaging table is compressed by a compression plate and collecting a tissue by inserting a biopsy needle into a position of a biopsy site calculated based on a radiation image through an opening portion of the compression plate. In addition, JP2011-024748A discloses a method of housing the collected tissue in a petri dish, disposing the petri dish on the compression plate in a state where the breast is compressed, performing radiography, performing examination as to whether or not the collected tissue is a desired tissue, and performing re-collection if necessary.

However, in a case of performing radiography of a collected sample such as a cell or a tissue while the breast is in a compressed state, it is required to dispose the sample at an appropriate position. Specifically, it is required to dispose the sample at a predetermined position within an irradiation range of radiation such that shadows of respective devices, instruments, the breast, and the like are not reflected. In addition, it is also required to prevent the sample from moving until the imaging is completed.

However, in the related art, since an operator places the sample at his/her discretion, the sample may be shifted from an appropriate position. In addition, even though the sample is initially placed at an appropriate position, the sample may be shifted during the imaging due to movement of the operator and the subject during the imaging process. Further, depending on a position of a biopsy site, the imaging table may be inclined to collect the sample and perform radiography in a state where the breast is compressed, and the sample may fall off due to the influence of gravity. In these cases, the accuracy of radiography of the sample is deteriorated.

SUMMARY

The present disclosure provides a mammography apparatus and a sample imaging assistance set capable of improving the accuracy of radiography of a sample.

According to a first aspect of the present disclosure, there is provided a mammography apparatus comprising: an imaging table that has a placement surface on which a breast is placed; a protective cover that includes a first magnetic object at a predetermined first position and is mounted on the placement surface; and a sample tray that includes a second magnetic object and a housing part of a sample and is placed on the placement surface via the protective cover, the second magnetic object being attracted to the first magnetic object by a magnetic force, in which the sample tray is configured to be magnetically attached to the predetermined first position of the protective cover by the first magnetic object and the second magnetic object.

In the aspect, the protective cover may include the first magnetic objects at each of a plurality of the predetermined first positions disposed at intervals, and the sample tray may include a plurality of the second magnetic objects disposed to correspond to a disposition of the plurality of predetermined first positions.

In the aspect, the protective cover may include a tray placement region which includes the predetermined first position and on which the sample tray is placed in a state where the protective cover is mounted on the placement surface, and the tray placement region may be a region on an end part side from a center in a width direction orthogonal to a depth direction from a chest wall toward a nipple of the breast placed on the protective cover.

In the aspect, the protective cover may include a tray placement region which includes the predetermined first position and on which the sample tray is placed in a state where the protective cover is mounted on the placement surface, and the tray placement region may be a region on a chest wall side from a center in a depth direction from a chest wall toward a nipple of the breast placed on the protective cover.

In the aspect, the protective cover may include, in a state where the protective cover is mounted on the placement surface, an irradiation region which is irradiated with radiation, a non-irradiation region which is not irradiated with radiation, and a tray placement region on which the sample tray is placed and which includes the predetermined first position, and in the tray placement region, at least the predetermined first position may be included in the non-irradiation region, and a remaining region including the housing part may be included in the irradiation region.

In the aspect, the first magnetic object may be a magnetized object, and the second magnetic object may be a magnet.

In the aspect, the imaging table may include a third magnetic object at a predetermined second position on the placement surface, the protective cover may further include a fourth magnetic object which is attracted to the third magnetic object by a magnetic force, and the protective cover may be configured to be magnetically attached to the predetermined second position of the imaging table by the third magnetic object and the fourth magnetic object.

In the aspect, the first magnetic object and the fourth magnetic object may have different forms.

In the aspect, the protective cover may include a plurality of the first magnetic objects disposed at equal intervals and a plurality of the fourth magnetic objects disposed at equal intervals, and an interval between the plurality of the first magnetic objects may be different from an interval between the plurality of the fourth magnetic objects.

In the aspect, the third magnetic object may be a magnetized object, and the fourth magnetic object may be a magnet.

In the aspect, the mammography apparatus may further comprise: an irradiation unit that irradiates the placement surface with radiation; and a controller that controls the irradiation unit, in which the controller may control the irradiation unit such that at least a part of the housing part is irradiated with the radiation and at least a part of the breast is not irradiated with the radiation.

In the aspect, the controller may control the irradiation unit such that at least a part of the breast and the predetermined first position are not irradiated with the radiation.

According to a second aspect of the present disclosure, there is provided a mammography apparatus comprising: an imaging table that has a placement surface on which a breast is placed and includes a first magnetic object disposed at a predetermined first position on the placement surface; and a sample tray that includes a second magnetic object and a housing part of a sample and is placed on the placement surface, the second magnetic object being attracted to the first magnetic object by a magnetic force, in which the sample tray is configured to be magnetically attached to the predetermined first position of the imaging table by the first magnetic object and the second magnetic object.

According to a third aspect of the present disclosure, there is provided a sample imaging assistance set comprising: a protective cover that includes a first magnetic object and is mounted on a placement surface of a mammography apparatus on which a breast is placed; and a sample tray that includes a second magnetic object and a housing part of a sample, the second magnetic object being attracted to the first magnetic object by a magnetic force.

According to the above aspects, the mammography apparatus and the sample imaging assistance set of the present disclosure can improve the accuracy of radiography of the sample.

DETAILED DESCRIPTION

Hereinafter, an embodiment of the present disclosure will be described with reference to the drawings. First, a mammography apparatus 2 of the present embodiment will be described in detail using FIG. 1 and FIG. 2.

Figure 1:
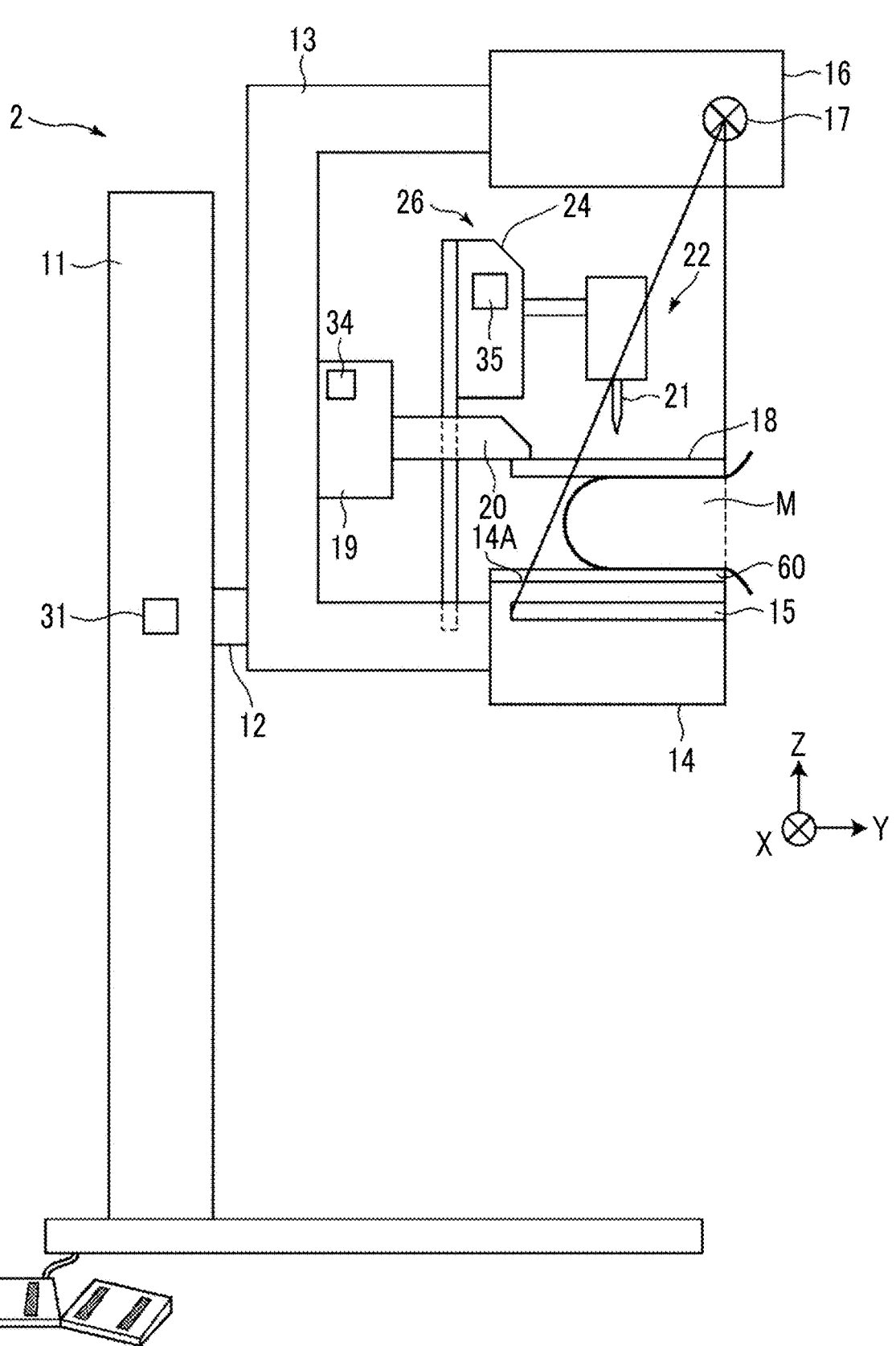
FIG. 1 is a schematic configuration diagram illustrating an example of a mammography apparatus.

FIG. 1 is a schematic configuration diagram illustrating an example of the mammography apparatus 2 according to the present embodiment. As illustrated in FIG. 1, in the mammography apparatus 2, a radiation housing unit 16 in which a radiation irradiator 17 is housed inside and an imaging table 14 are connected to an arm 13 to face each other.

An image recording medium such as a radiation detector 15 is set inside the imaging table 14 in a state of being housed in a recording medium holding portion such as a cassette. The arm 13 is attached to a base 11 with a C axis 12. In addition, the arm 13 is provided to the base 11 by attaching the C axis 12, which is the center of rotation, to a center position of the radiation detector 15 such that the center of rotation of the arm 13 is the center of the radiation detector 15 in an X direction (refer to FIG. 2).

The base 11 is provided with an operation unit 28 that receives an instruction for radiation irradiation from the radiation irradiator 17 and allows an operator to adjust a height of the imaging table 14 (that is, a height of the arm 13) and an inclination of the imaging table 14 (that is, an inclination of the arm 13), and with an arm controller 31 that moves the arm 13 vertically and rotationally according to an input from the operation unit 28. The arm controller 31 adjusts the inclination of the arm 13 by rotating the C axis 12 attached to the base 11, and adjusts the height of the imaging table 14 by vertically moving the arm 13.

At a center part of the arm 13, a compression plate 18 that is disposed above the imaging table 14 to hold and compress the breast M, a support portion 20 that supports the compression plate 18, and a moving mechanism 19 that moves the support portion 20 in a vertical direction along the arm 13. The position and compression pressure of the compression plate 18 are controlled by a compression plate controller 34.

Figure 2:
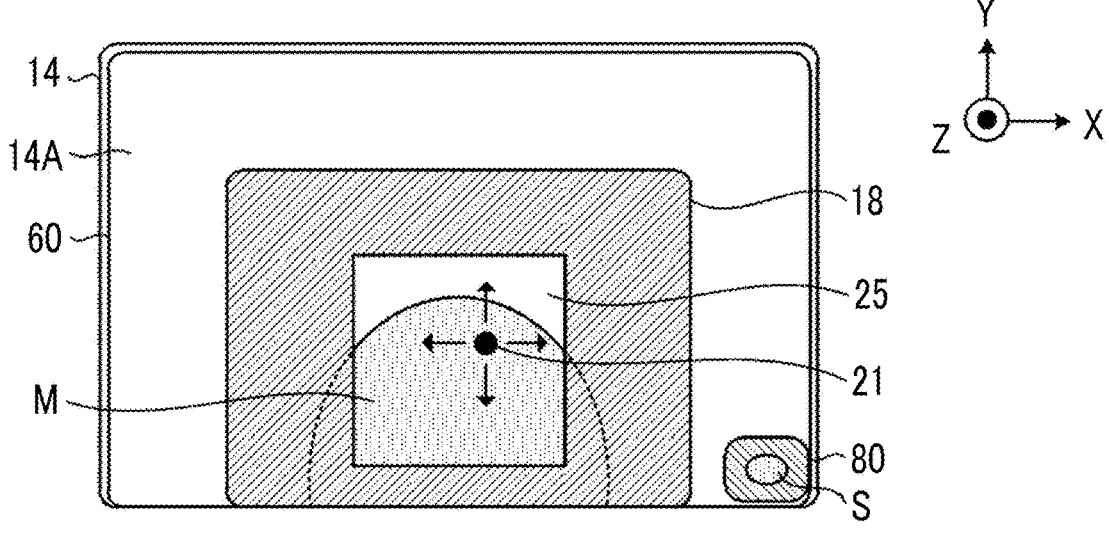
FIG. 2 is a schematic configuration diagram illustrating an example of a compression plate.

FIG. 2 is a schematic view of an example of a usage aspect of the mammography apparatus 2 as viewed from above the imaging table 14. As illustrated in FIG. 2, the imaging table 14 comprises a placement surface 14A on which the breast M is placed, and a protective cover 60 is mounted on the placement surface 14A to protect the imaging table 14 from contamination due to body fluid or the like of the subject. The breast M is placed on the protective cover 60, and the breast M is compressed by the compression plate 18. The compression plate 18 comprises an opening portion 25 such that it is possible to perform a biopsy in a state where the breast M is fixed by the imaging table 14 and the compression plate 18. A size of the opening portion 25 is, for example, approximately 10×10 cm square.

In addition, at an end portion of the imaging table 14, a sample tray 80 comprising a housing part 82 for housing a sample S collected by a biopsy is placed on the placement surface 14A via the protective cover 60. The housing part 82 has a cross-sectional shape of a recess shape, and can house the sample S therein. Note that FIG. 2 illustrates an example in which the sample tray 80 is placed on a right side and a chest wall side of the breast M. On the other hand, the placement position of the sample tray 80 is not limited thereto, and may be a position that does not interfere with the breast M, the compression plate 18, and the like.

Preferably, the protective cover 60 and the sample tray 80 are formed of a material that is excellent in radiation transmittance and is excellent in strength such as falling strength and compression strength. As such a material, for example, resin, such as polymethylpentene (PMP), polycarbonate (PC), acryl, polypropylene (PP), and polyethylene terephthalate (PET), can be used.

A biopsy unit 26 comprises a biopsy needle 21 that is inserted into the breast M and a biopsy needle unit 22, and further comprises a moving mechanism 24 that moves the biopsy needle unit 22 in X, Y, and Z directions. A position of a distal end of the biopsy needle 21 of the biopsy needle unit 22 is controlled by a needle position controller 35 of the moving mechanism 24. Note that, in FIG. 2, a horizontal direction is the X direction, a vertical direction is the Y direction, and a direction perpendicular to an XY plane is the Z direction.

Note that, in the mammography apparatus 2, scout images captured from two directions to include a target region of the breast M to be biopsied are acquired before performing puncture. The scout image is an image viewed from different viewpoints in order to check the position to be pathologically examined. For example, two partial images, which are obtained by performing imaging with the radiation irradiator 17 from directions inclined left and right from the direction along the arm 13, are used as the scout images. From a deviation of a target included in the two scout images, a distance z from a bottom surface of the compression plate 18 (a side that contacts and presses the breast) to the target and the position of the target on the XY plane are obtained, and thus, three-dimensional position information of the target can be obtained.

In a case where the needle position controller 35 of the biopsy unit 26 receives the positional information of the target, the needle position controller 35 moves the position of the distal end of the biopsy needle 21 to the position of the target, and performs the puncture on the breast M with the biopsy needle 21.

Figure 3:
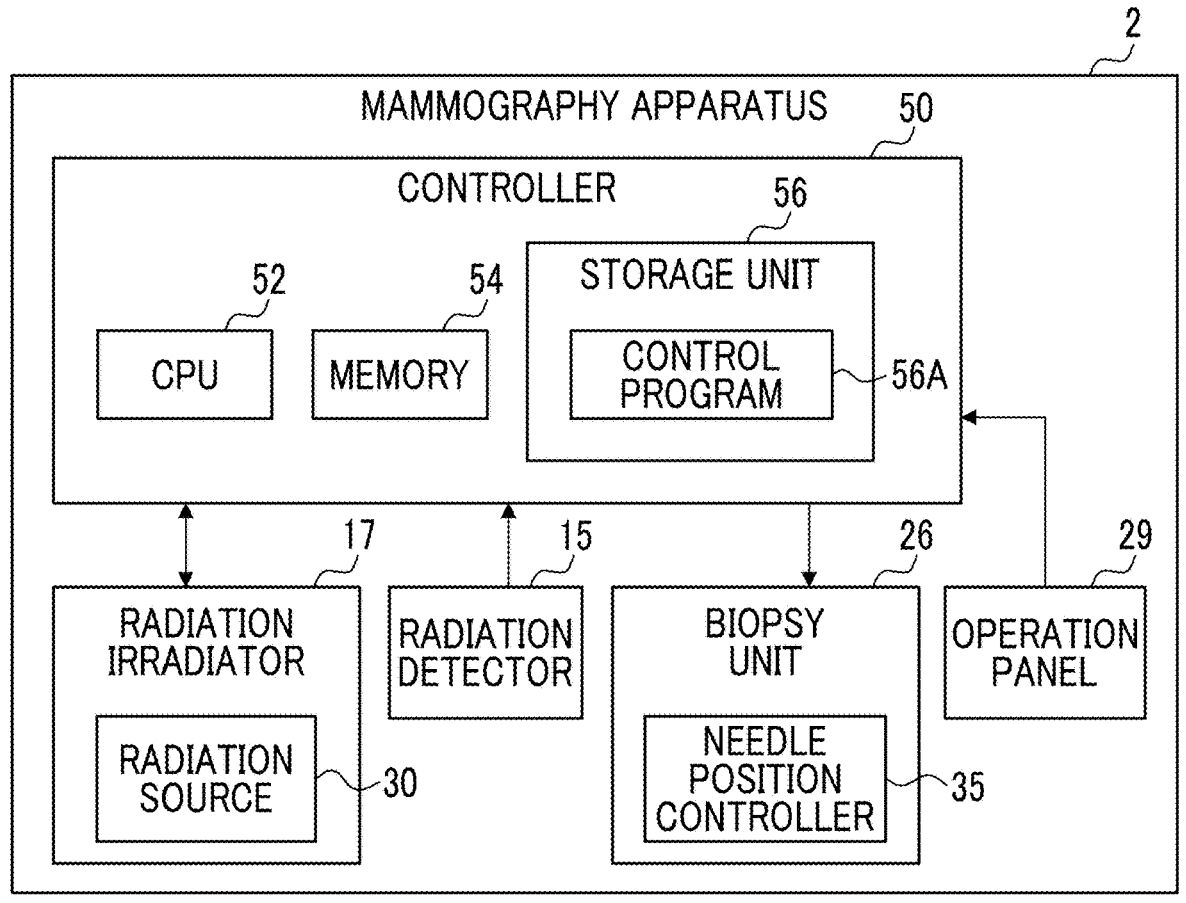
FIG. 3 is a block diagram illustrating an example of an electrical configuration of the mammography apparatus.

Next, an electrical configuration of the mammography apparatus 2 will be described with reference to FIG. 3. FIG. 3 is a block diagram illustrating an example of the electrical configuration of the mammography apparatus 2. As illustrated in FIG. 3, the mammography apparatus 2 includes an operation panel 29 and a controller 50 in addition to the radiation detector 15, the radiation irradiator 17, and the biopsy unit 26 described above. The controller 50 is connected to the radiation irradiator 17, the radiation detector 15, the biopsy unit 26, and the operation panel 29. The radiation irradiator 17 is an example of an irradiation unit that irradiates the placement surface 14A according to the present disclosure with radiation.

The radiation detector 15 receives irradiation of radiation carrying image information and records the image information, and outputs the recorded image information. For example, the radiation detector 15 is configured as a flat panel detector (FPD) that includes a radiation-sensitive layer and converts radiation into digital data and outputs the digital data. In a case where the radiation detector 15 is irradiated with radiation, the radiation detector 15 outputs the image information indicating the radiation image to the controller 50. For example, the radiation detector 15 receives the radiation passing through the breast M or the sample S (details will be described later) housed in the sample tray 80, and thus image information indicating a radiation image of the breast M or the sample S is obtained.

The needle position controller 35 provided in the biopsy unit 26 drives the biopsy unit 26 in response to an instruction of the controller 50. Specifically, the biopsy needle 21 is moved to a designated position, and is held in a state of being inclined at an insertion angle.

The operation panel 29 has a function of setting various kinds of operation information such as exposure conditions and posture information, various operation instructions, and the like. The exposure conditions that are set in the operation panel 29 include, for example, information such as a tube voltage, a tube current, an irradiation time, and posture information. The posture information designated in the operation panel 29 includes information representing an imaging position (imaging posture, angle) in a case of imaging the breast M from a plurality of directions.

The controller 50 has a function of controlling the operation of the entire mammography apparatus 2, and is configured to include a central processing unit (CPU) 52 as a processor, a memory 54 including a read only memory (ROM) and a random access memory (RAM), a non-volatile storage unit 56 including a hard disk drive (HDD), a flash memory, and the like. A storage unit 56 stores a control program 56A that controls an operation of the entire mammography apparatus 2. The CPU 52 reads out the control program 56A from the storage unit 56, loads the read-out control program 56A into the memory 54, and executes the loaded control program 56A.

In a case where the controller 50 receives an irradiation instruction from the operator via the operation panel 29 (exposure switch), the controller 50 causes a radiation source 30 provided in the radiation irradiator 17 to irradiate an upper surface of the imaging table 14 with radiation according to an imaging menu which is set based on the designated exposure conditions. That is, the radiation image is captured by irradiating the imaging part (the breast M or the sample S) placed on the placement surface 14A with radiation.

Note that, in order to reduce a risk of radiation exposure to the subject, preferably, the breast M is not irradiated with radiation in a case of performing radiography of the sample S. Specifically, in a case of performing radiography of the sample S, preferably, the controller 50 controls the radiation irradiator 17 such that the sample S is irradiated with radiation at at least a part of the housing part 82 (refer to FIG. 4) of the sample tray 80 and at least a part of the breast M is not irradiated with radiation.

In addition, the sample tray 80 according to the present embodiment is configured to be magnetically attached to a first predetermined position of the protective cover 60 by a first magnetic object 91 and a second magnetic object 92 (details will be described later). In order to suppress an influence of these magnetic objects on the radiation image, for example, an occurrence of artifacts, preferably, the first predetermined position (that is, the first magnetic object 91 and the second magnetic object 92) is not irradiated with the radiation. Specifically, in a case of performing radiography of the sample S, preferably, the controller 50 controls the radiation irradiator 17 such that at least a part of the breast M and the first predetermined position are not irradiated with the radiation.

Further, in a case of performing tomosynthesis imaging in which imaging is performed from a plurality of directions, the controller 50 adjusts a posture of the arm 13 such that the radiation irradiator 17 is positioned above the upper surface of the imaging table 14. In addition, the controller 50 rotates the arm 13 to move the radiation irradiator 17 from a predetermined initial angle in an arc shape by a predetermined angle, and causes the radiation source 30 provided in the radiation irradiator 17 to individually irradiate the upper surface of the imaging table 14 with the radiation at different angles based on the imaging conditions. Thereby, a plurality of radiation images can be obtained.

Note that various types of operation information such as the exposure conditions and the posture information, various types of operation instructions, and the like are not limited to being set by the operator using the operation panel 29 and, for example, may be stored in advance in a storage unit. In addition, for example, the information, the instruction, and the like may be obtained from another control device such as a radiology information system (RIS).

With the above configuration, the mammography apparatus 2 according to the present embodiment can perform radiography of the sample S collected from the breast M while the breast M is in the compressed state. Therefore, based on the radiation image of the sample S, it is possible to check whether or not the sample S includes a desired tissue in a state where the breast M is in the compressed state, and to recollect a sample S if necessary.

Meanwhile, in a case of performing radiography of the collected sample S while the breast M is in the compressed state, it is required to place the sample S at an appropriate position. Specifically, it is desired that the sample S is placed at a predetermined position within an irradiation range of the radiation such that shadows of the respective devices, instruments, the breast M, and the like are not reflected. In addition, it is desired that the sample S is not moved until the imaging is completed.

On the other hand, in a case where the operator places the sample S on the imaging table 14 at his/her discretion, the sample S may be shifted from an appropriate position. In addition, even though the sample S is initially placed at an appropriate position, the sample S may be shifted during the imaging due to movement of the operator and the subject during the imaging process. In addition, depending on a position of a biopsy site, the imaging table 14 (that is, the arm 13) may be inclined to collect the sample S and perform radiography, and the sample S may not be placed on the imaging table 14 or may fall off due to the influence of gravity. In these cases, the accuracy of radiography of the sample S may be deteriorated.

Therefore, in the mammography apparatus 2 according to the present embodiment, the sample tray 80 housing the sample S is adsorbed to the protective cover 60 mounted on the placement surface 14A of the imaging table 14 by a magnetic force, and thus, alignment and fixation of the sample tray 80 can be easily realized. Hereinafter, the detailed configurations of the imaging table 14, the protective cover 60, and the sample tray 80 will be described with reference to FIG. 4 to FIG. 6.

Figure 4:
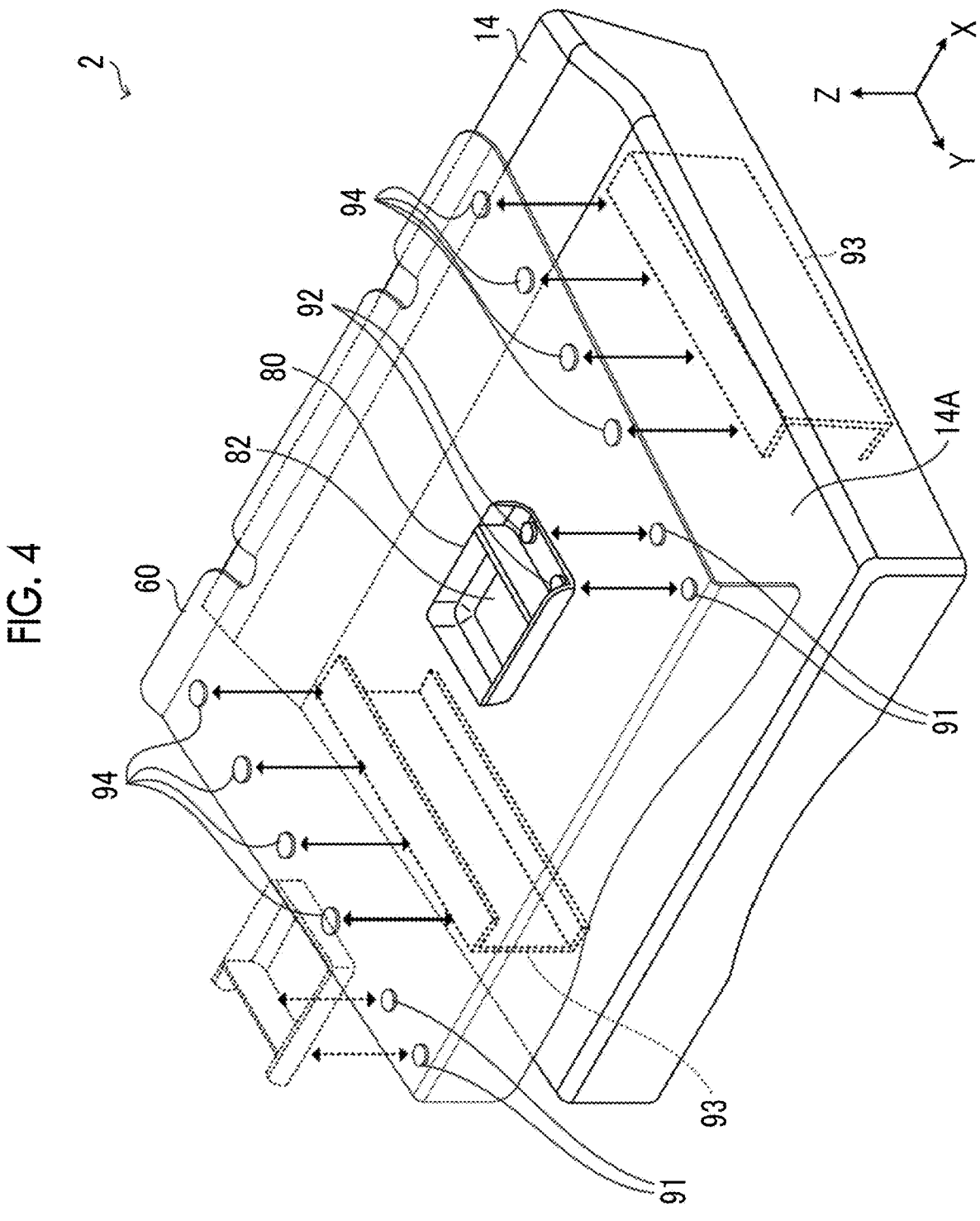
FIG. 4 is an exploded perspective view of an imaging table, a protective cover, and a sample tray.
Figure 5:
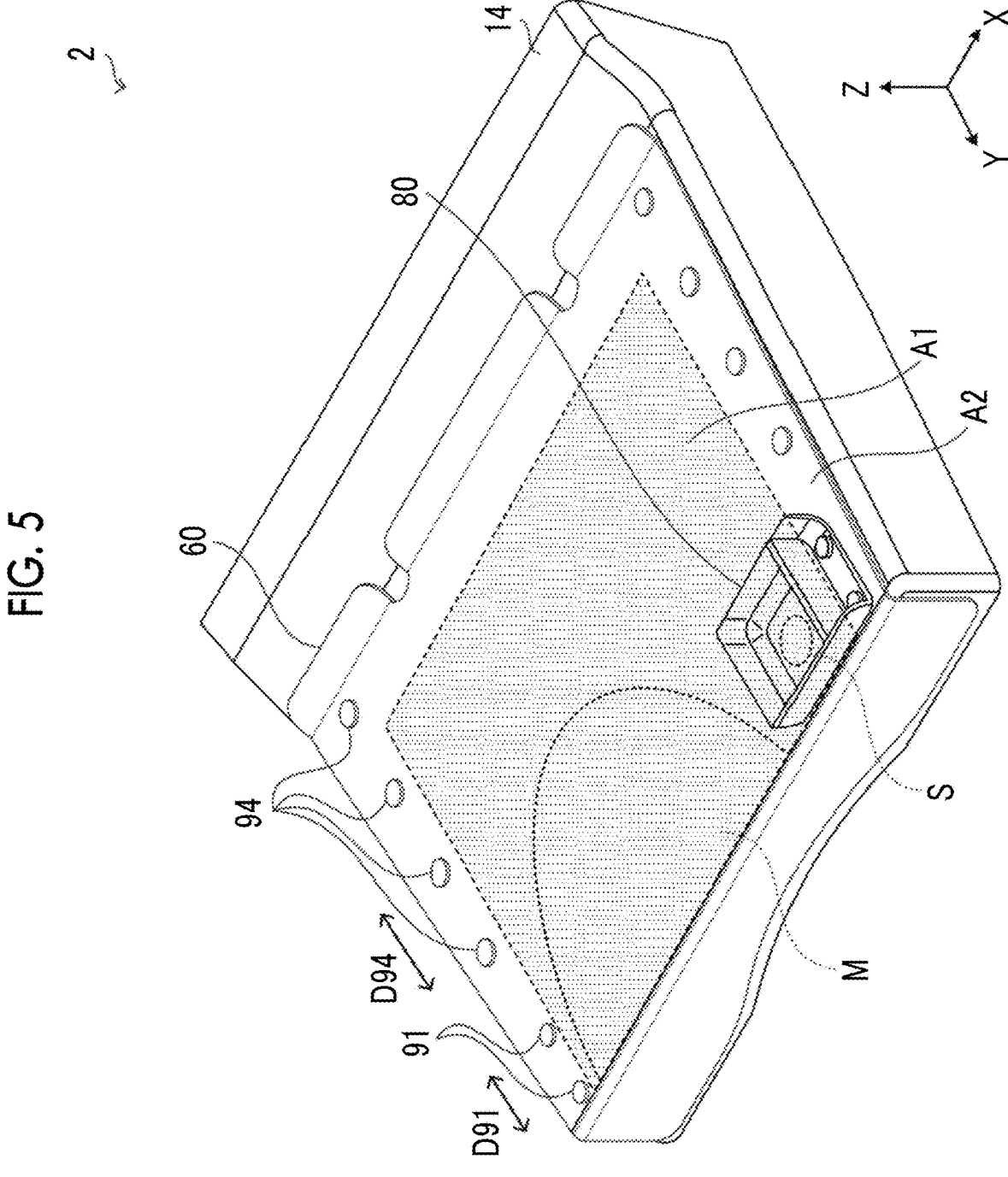
FIG. 5 is a perspective view of an imaging table, a protective cover, and a sample tray.

FIG. 4 is an exploded perspective view illustrating an example of a state where the imaging table 14, the protective cover 60, and the sample tray 80 are disassembled. FIG. 5 is a perspective view illustrating an example of a state where the imaging table 14, the protective cover 60, and the sample tray 80 are combined and used as the mammography apparatus 2. FIG. 5 illustrates the position of the breast M placed on the imaging table 14, the position of the sample S, and the irradiation region A1 of the radiation.

As illustrated in FIG. 4, the protective cover 60 comprises a first magnetic object 91 at a first predetermined position. In addition, the sample tray 80 comprises a second magnetic object 92 that is attracted to the first magnetic object 91 of the protective cover 60 by a magnetic force. That is, the sample tray 80 is configured to be magnetically attached to the first predetermined position of the protective cover 60 by the first magnetic object 91 and the second magnetic object 92. Here, the first predetermined position is a predetermined position on the protective cover 60, and is a position at which the imaging of the sample S housed in the sample tray 80 can be appropriately performed in a case where the sample tray 80 is placed on the position.

With such a configuration, the sample tray 80 can be magnetically attached to the first predetermined position (the position suitable for imaging the sample S) by the first magnetic object 91 of the protective cover 60 and the second magnetic object 92 of the sample tray 80. Therefore, the positioning of the sample tray 80 on the protective cover 60 can be easily performed, and the sample S can be placed at an appropriate position regardless of the operator's discretion. In addition, the protective cover 60 and the sample tray 80 are magnetically attached to each other, and thus, the sample tray 80 is less likely to be shifted. Therefore, radiography of the sample S can be stably performed. In addition, in a case where the magnetic force is sufficiently strong, even in a case where the sample tray 80 is placed on the protective cover 60 in a state where the imaging table 14 (that is, the arm 13) is inclined, the sample tray 80 does not fall down by gravity. Therefore, a degree of freedom in the posture of the subject and the positioning of the breast M is improved, and it is possible to collect the sample S from a site at which the collection is difficult in the related art.

In addition, as illustrated in FIG. 4, preferably, the protective cover 60 comprises the first magnetic objects 91 at each of a plurality of predetermined first positions disposed at intervals. In this case, the sample tray 80 is configured to comprise a plurality of second magnetic objects 92 that are disposed to correspond to the disposition of the plurality of predetermined first positions on the protective cover 60 side. In the example in FIG. 4, the protective cover 60 comprises two first magnetic objects 91, and the sample tray 80 also comprises two second magnetic objects 92 in correspondence with the first magnetic objects 91. The interval between the two first magnetic objects 91 and the interval between the two second magnetic objects 92 are the same.

As described above, with the configuration in which a plurality of combinations of the corresponding first magnetic objects 91 and the corresponding second magnetic objects 92 are provided, the protective cover 60 and the sample tray 80 can be magnetically attached to each other at a plurality of positions (each of the plurality of predetermined first positions). Therefore, the sample tray 80 can be placed on the protective cover 60 at a more accurate position and in a more accurate direction as compared with a case where the sample tray 80 is magnetically attached at one place. Thus, the accuracy of radiography of the sample S can be improved. In addition, the sample tray 80 is less likely to be shifted, and thus radiography of the sample S can be more stably performed.

Next, a preferable position at which the sample tray 80 is placed on the protective cover 60 will be described. Hereinafter, in a state where the protective cover 60 is mounted on the placement surface 14A of the imaging table 14, a region on the protective cover 60 on which the sample tray 80 is placed and which includes the predetermined first position is referred to as a "tray placement region".

As illustrated in FIG. 5, preferably, the tray placement region is a region on the end part side (that is, the outer side) from a center in a width direction (X direction in FIG. 5) orthogonal to a depth direction (a direction opposite to the Y direction in FIG. 5) from the chest wall toward the nipple of the breast M that is placed on the protective cover 60. In the example of FIG. 5, the breast M is placed to be biased to the left side as viewed from the subject, and the sample tray 80 is placed on the right end part side as viewed from the subject. In this way, the sample tray 80 is placed on the end part side from the center part at which the breast M is placed, and thus, it is possible to reduce a risk of radiation exposure of the subject in a case of performing radiography of the sample S.

In addition, in the examples of FIG. 4 and FIG. 5, the tray placement regions are provided on both sides in the left-right direction (the X direction in FIG. 5) as viewed from the subject, and any of the left and right tray placement regions can be selectively used. In FIG. 4, the sample tray 80 placed in the tray placement region on the left side as viewed from the subject is illustrated by a dotted line. With such a configuration, a degree of freedom of the placement position of the sample tray 80 is improved. For example, the sample tray 80 can be placed on the preferable end part side depending on whether the breast M is a right breast or a left breast and the posture of the subject.

Figure 6:
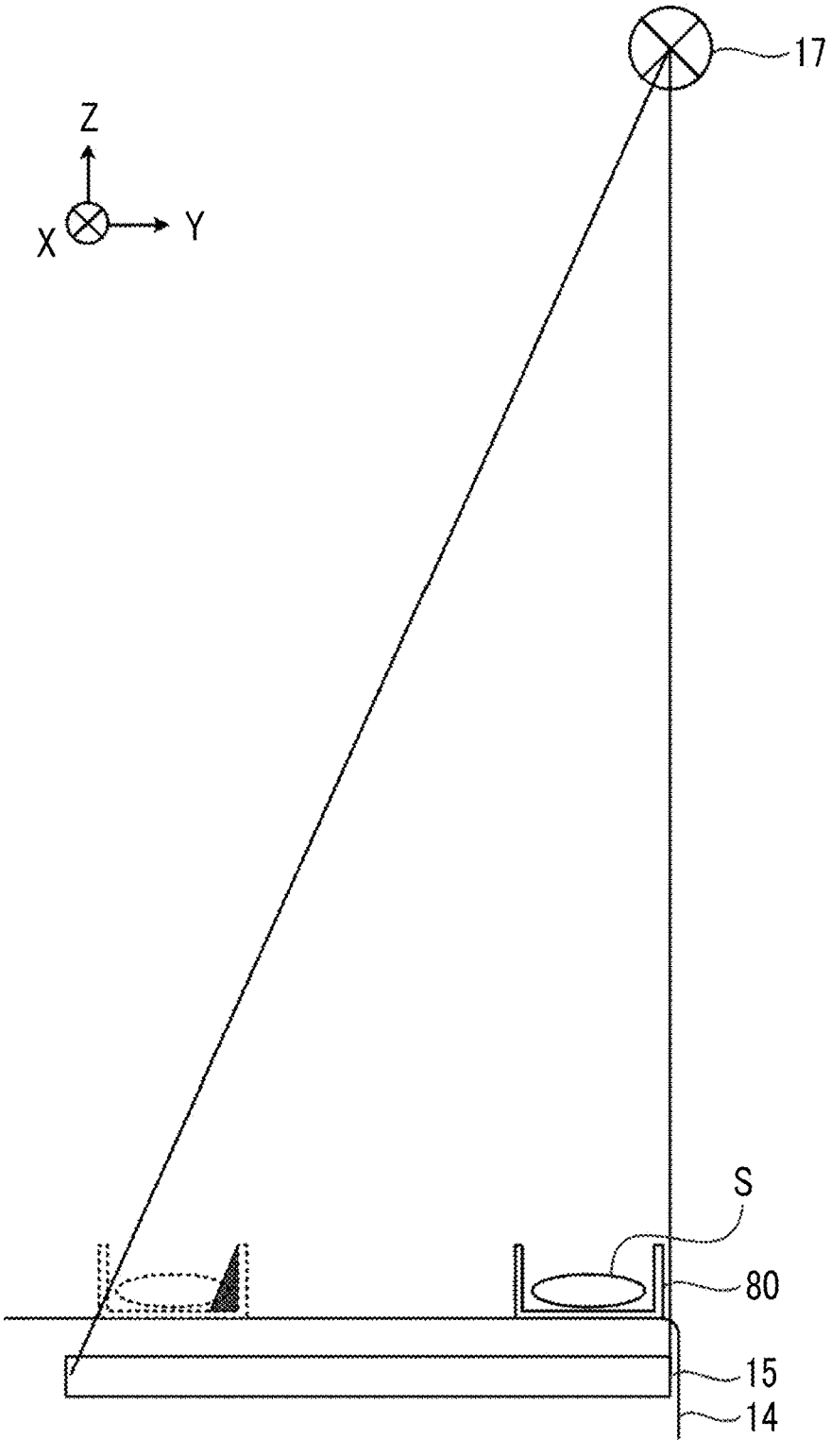
FIG. 6 is a diagram for explaining an appropriate placement position of the sample tray.

In addition, as illustrated in FIG. 5 and FIG. 6, preferably, the tray placement region is a region on the chest wall side from the center in the depth direction (the direction opposite to the Y direction in FIG. 5) from the chest wall toward the nipple of the breast M that is placed on the protective cover 60. FIG. 6 is a diagram illustrating the sample tray 80 as viewed from the left side of the subject. As illustrated in FIG. 6, generally, in the mammography apparatus 2, the radiation irradiator 17 is disposed at a position at which the breast M can be irradiated with the radiation at a radiation angle close to a vertical angle.

As illustrated by a solid line in FIG. 6, the sample tray 80 is placed on the chest wall side (that is, the side close to the subject), and thus, the sample S can be irradiated with the radiation at a radiation angle close to a vertical angle as in the case of imaging the breast M. Therefore, an appropriate radiation image of the sample S can be obtained. On the other hand, as indicated by a dotted line in FIG. 6, in a case where the sample tray 80 is placed on a side opposite to the chest wall side in the depth direction (that is, a side far from the subject), the irradiation angle of the radiation with which the sample S is irradiated is not vertical. In this case, as illustrated in FIG. 6, a side wall of the sample tray 80 may be reflected in the radiation image as so-called vignetting.

In addition, as illustrated in FIG. 5, the protective cover 60 includes an irradiation region A1 that is irradiated with radiation and a non-irradiation region A2 that is not irradiated with radiation in a state of being mounted on the placement surface 14A of the imaging table 14. In this case, in the tray placement region, preferably, at least the predetermined first position is included in the non-irradiation region A2, and the remaining region including the housing part 82 of the sample S is included in the irradiation region A1. That is, preferably, the sample S is reflected in the radiation image, and the first magnetic object 91 and the second magnetic object 92 are not reflected in the radiation image. The first magnetic object 91 and the second magnetic object 92 are disposed in the non-irradiation region A2 of the radiation, and thus, it is possible to suppress an influence of the magnetic objects on the radiation image, for example, an occurrence of an artifact.

Although alignment and fixation of the protective cover 60 and the sample tray 80 using the magnetic force have been described above, alignment and fixation of the placement surface 14A of the imaging table 14 and the protective cover 60 using the magnetic force may be performed. For example, as illustrated in FIG. 4, the imaging table 14 may comprise a third magnetic object 93 at a predetermined second position on the placement surface 14A. The protective cover 60 may further comprise a fourth magnetic object 94 that is attracted to the third magnetic object 93 of the imaging table 14 by the magnetic force. That is, the protective cover 60 may be configured to be magnetically attached to the predetermined second position of the imaging table 14 by the third magnetic object 93 and the fourth magnetic object 94. Here, the predetermined second position is a position that is set in advance on the placement surface 14A of the imaging table 14, and is a position at which the position relationship between the irradiation region A1 of the radiation, the sample tray 80, the breast M, and the like can be aligned in a case where the protective cover 60 is mounted in accordance with the position.

As the first magnetic object 91, the second magnetic object 92, the third magnetic object 93, and the fourth magnetic object 94, for example, magnetic metals such as iron, nickel, and cobalt, and magnetic oxides such as ferrite and magnetite can be appropriately applied. A magnetized object is an object that does not have magnetic properties by itself or has a weak magnetic force compared to a magnet, and is, for example, a ferromagnetic object.

The fact that the first magnetic object 91 and the second magnetic object 92 are attracted to each other by the magnetic force means that at least one of the first magnetic object 91 or the second magnetic object 92 is a magnet. That is, the first magnetic object 91 and the second magnetic object 92 are respectively a combination of a magnetized object and a magnet, a magnet and a magnetized object, or magnets having different polarities. Note that, as illustrated in FIG. 4, in a case where there are a plurality of combinations of the first magnetic object 91 and the second magnetic object 92 corresponding to each other, which of the first magnetic object 91 and the second magnetic object 92 is made of a magnet may be different for each combination.

Preferably, the first magnetic object 91 of the protective cover 60 is a magnetized object, and the second magnetic object 92 of the sample tray 80 is a magnet. The mammography apparatus 2 can also be used for normal mammography imaging without biopsy, and it is considered that only the protective cover 60 can be used from the viewpoint of hygiene even without using the sample tray 80. The first magnetic object 91 of the protective cover 60 is made of a magnetized object instead of a magnet, and thus, inconvenience caused by the magnetic force, for example, adsorption of an unintended magnetic object such as dust can be prevented.

The fact that the third magnetic object 93 and the fourth magnetic object 94 are attracted to each other by the magnetic force means that at least one of the third magnetic object 93 or the fourth magnetic object 94 is a magnet. That is, the third magnetic object 93 and the fourth magnetic object 94 are respectively a combination of a magnetized object and a magnet, a magnet and a magnetized object, or magnets having different polarities. Note that, as illustrated in FIG. 4, in a case where there are a plurality of combinations of the third magnetic object 93 and the fourth magnetic object 94 corresponding to each other, which of the third magnetic object 93 and the fourth magnetic object 94 is made of a magnet may be different for each combination.

Preferably, the third magnetic object 93 of the imaging table 14 is a magnetized object, and the fourth magnetic object 94 of the protective cover 60 is a magnet. The mammography apparatus 2 can also be used for normal mammography imaging without biopsy. In this case, it is considered that the breast M is directly placed on the imaging table 14 without using the sample tray 80 or the protective cover 60. The third magnetic object 93 of the imaging table 14 is made of a magnetized object instead of a magnet, and thus, inconvenience caused by the magnetic force, for example, adhesion of an unintended magnetic object such as dust can be prevented.

In addition, in the protective cover 60, preferably, the first magnetic object 91 for adsorbing the sample tray 80 and the fourth magnetic object for adsorbing the imaging table 14 can be distinguished from each other. For example, at least one form of a size, a shape, a color, or a pattern may be different. In addition, for example, as illustrated in FIG. 4 and FIG. 5, in a case where the protective cover 60 comprises a plurality of first magnetic objects 91 disposed at equal intervals and a plurality of fourth magnetic objects 94 disposed at equal intervals, the interval between the plurality of first magnetic objects 91 and the interval between the plurality of fourth magnetic objects 94 may be different from each other.

As an example, in FIG. 4 and FIG. 5, the first magnetic object 91 and the fourth magnetic object 94 have different sizes. In addition, an interval D91 between the first magnetic objects 91 and an interval D94 between the fourth magnetic objects 94 are different from each other. In this way, by changing the form or the interval, the first magnetic object 91 and the fourth magnetic object 94 can be distinguished from each other. Therefore, it is possible to prevent the sample tray 80 from being placed at an incorrect position (the fourth magnetic object 94). Note that, in FIG. 4 and FIG. 5, a configuration in which two first magnetic objects 91 and two second magnetic objects 92 are disposed and four third magnetic objects 93 and four fourth magnetic objects 94 are disposed is illustrated. On the other hand, the present disclosure is not limited thereto. The numbers, the intervals, and the dispositions of the first magnetic objects 91, the second magnetic objects 92, the third magnetic objects 93, and the fourth magnetic objects 94 can be appropriately changed. For example, four first magnetic objects 91 and four second magnetic objects 92 may be arranged in a rectangular shape, three first magnetic objects 91 and three second magnetic objects 92 may be arranged in an L-shape, or a plurality of first magnetic objects 91 and a plurality of second magnetic objects 92 may be arranged at different intervals.

In addition, FIG. 4 illustrates an example in which a plate as the third magnetic object 93 is embedded inside the imaging table 14 so as not to be visible from the outside. On the other hand, the present disclosure is not limited thereto. The third magnetic object 93 may be provided to have a magnetic force only for attracting the fourth magnetic object 94 of the protective cover 60. Therefore, for example, a form in which the third magnetic object 93 such as a plate or a magnet is adhered onto the placement surface 14A (that is, visible from the outside) may be adopted.

As described above, the mammography apparatus 2 according to the present embodiment comprises the imaging table 14 that has the placement surface 14A on which the breast M is placed, the protective cover 60 that comprises the first magnetic object 91 at the predetermined first position and is mounted on the placement surface 14A, and the sample tray 80 that comprises the second magnetic object 92, which is attracted to the first magnetic object 91 by a magnetic force, and the housing part 82 of the sample S and is placed on the placement surface 14A via the protective cover 60. The sample tray 80 is configured to be magnetically attached to the predetermined first position of the protective cover 60 by the first magnetic object 91 and the second magnetic object 92.

That is, with the mammography apparatus 2 according to the present embodiment, in a case of performing radiography of the sample S collected from the breast M while the breast M is in the compressed state, the sample S can be placed at an appropriate position. Therefore, shadows of the respective devices, instruments, the breast M, and the like are not reflected, and the accuracy of the radiography of the sample S can be improved.

Further, even in a case where the imaging table 14 (that is, the arm 13) is inclined to collect the sample S and to perform radiography, the sample tray 80 is magnetically attached to the protective cover 60, and thus, it is possible to prevent the sample tray 80 from sliding down due to the influence of gravity. Therefore, a degree of freedom in the posture of the subject and the positioning of the breast M is improved. Thus, it is possible to collect the sample S from a site at which the collection is difficult in the related art, and the accuracy of the radiography of the sample S can be improved.

Figure 7:
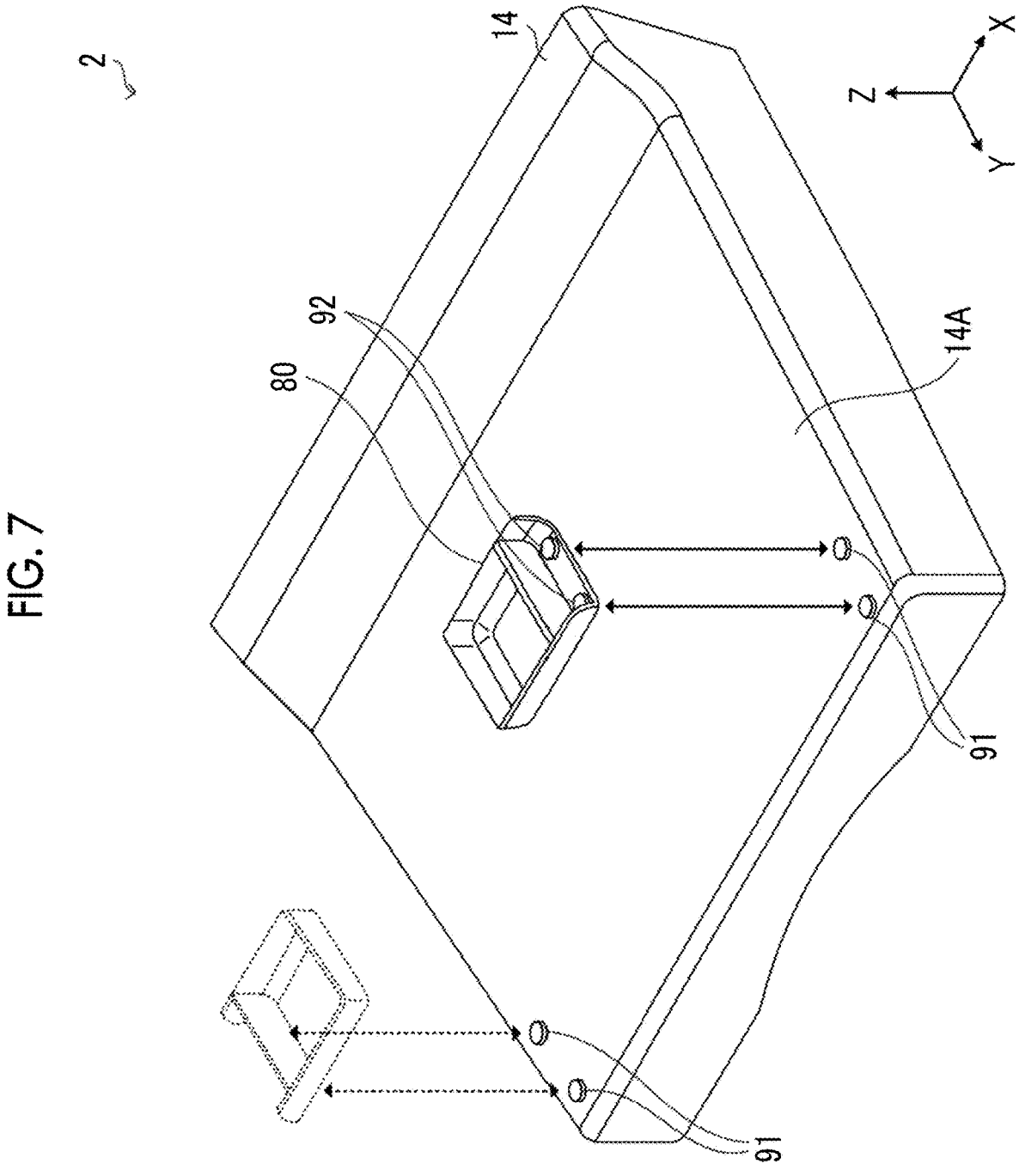
FIG. 7 is an exploded perspective view of an imaging table and a sample tray.

Note that, in the embodiment, the configuration in which the protective cover 60 is mounted on the placement surface 14A of the imaging table 14 and the sample tray 80 is placed on the protective cover 60 has been described. On the other hand, the present disclosure is not limited thereto. For example, as illustrated in FIG. 7, the first magnetic object 91 may be provided on the imaging table 14 instead of the protective cover 60, and the imaging table 14 and the sample tray 80 may be directly and magnetically attached to each other. In this case, a protective cover that does not block a magnetic force to prevent dirt may be mounted or may not be mounted on the placement surface 14A of the imaging table 14.

Specifically, the mammography apparatus 2 according to another embodiment of the present disclosure comprises an imaging table 14 that has a placement surface 14A on which the breast M is placed and comprises a first magnetic object 91 disposed at a predetermined first position on the placement surface 14A, and a sample tray 80 that comprises a second magnetic object 92 which is attracted to the first magnetic object 91 by a magnetic force and a housing part 82 of the sample S and is placed on the placement surface 14A. The sample tray 80 is configured to be magnetically attached to the predetermined first position of the imaging table 14 by the first magnetic object 91 and the second magnetic object 92. Even with such an embodiment, the accuracy of radiography of the sample S can be improved.

In addition, the technology of the present disclosure can also be applied to an existing mammography apparatus (that is, a mammography apparatus in which the imaging table 14 does not comprise the third magnetic object 93). For example, a sample imaging assistance set according to another embodiment of the present disclosure includes a protective cover 60 that comprises a first magnetic object 91 and is mounted on a placement surface 14A of the mammography apparatus on which the breast M is placed, and a sample tray 80 that comprises a second magnetic object 92 which is attracted to the first magnetic object 91 by a magnetic force and a housing part 82 of the sample S. That is, in any mammography apparatus, in a case where there is a combination of the protective cover 60 and the sample tray 80, alignment of the sample S can be easily performed in a case of performing radiography of the sample S, and the accuracy of radiography of the sample S can be improved.

Note that, in the above-described embodiment, for example, as a hardware structure of a processing unit that executes various types of processing, such as the controller 50, the following various processors can be used. As described above, the various processors include, in addition to the CPU that is a general-purpose processor that executes software (program) to function as various processing units, a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by one of the various processors, or may be configured by a combination of the same or different types of two or more processors (for example, a combination of a plurality of FPGAs or a combination of the CPU and the FPGA). In addition, a plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that realizes the function of the entire system including the plurality of processing units by one integrated circuit (IC) chip is used may be adopted. In this manner, the various processing units are configured by using one or more various processors as a hardware structure.

Further, as the hardware structure of the various processors, more specifically, an electric circuit (circuitry) in which circuit elements such as semiconductor elements are combined may be used.

In addition, in the above embodiment, the form in which the control program 56A is stored (installed) in advance in the storage unit 56 of the mammography apparatus 2 has been described. On the other hand, the present disclosure is not limited thereto. The program may be provided in a form of being recorded on a recording medium, such as a compact disc read only memory (CD-ROM), a digital versatile disc read only memory (DVD-ROM), and a Universal Serial Bus (USB) memory. Further, the program may be downloaded from an external device via a network.

From the above description, the invention described in following Appendices can be understood.

APPENDIX 1

A mammography apparatus comprising:
an imaging table that has a placement surface on which a breast is placed;
a protective cover that includes a first magnetic object at a predetermined first position and is mounted on the placement surface; and
a sample tray that includes a second magnetic object and a housing part of a sample and is placed on the placement surface via the protective cover, the second magnetic object being attracted to the first magnetic object by a magnetic force,
in which the sample tray is configured to be magnetically attached to the predetermined first position of the protective cover by the first magnetic object and the second magnetic object.

APPENDIX 2

The mammography apparatus according to Appendix 1,
in which the protective cover includes the first magnetic objects at each of a plurality of the predetermined first positions disposed at intervals, and
the sample tray includes a plurality of the second magnetic objects disposed to correspond to a disposition of the plurality of predetermined first positions.

APPENDIX 3

The mammography apparatus according to Appendix 1 or 2,
in which the protective cover includes a tray placement region which includes the predetermined first position and on which the sample tray is placed in a state where the protective cover is mounted on the placement surface, and
the tray placement region is a region on an end part side from a center in a width direction orthogonal to a depth direction from a chest wall toward a nipple of the breast placed on the protective cover.

APPENDIX 4

The mammography apparatus according to any one of Appendixes 1 to 3, in which the protective cover includes a tray placement region which includes the predetermined first position and on which the sample tray is placed in a state where the protective cover is mounted on the placement surface, and
the tray placement region is a region on a chest wall side from a center in a depth direction from a chest wall toward a nipple of the breast placed on the protective cover.

APPENDIX 5

The mammography apparatus according to any one of Appendixes 1 to 4,
in which the protective cover includes, in a state where the protective cover is mounted on the placement surface, an irradiation region which is irradiated with radiation, a non-irradiation region which is not irradiated with radiation, and
a tray placement region on which the sample tray is placed and which includes the predetermined first position, and
in the tray placement region, at least the predetermined first position is included in the non-irradiation region, and a remaining region including the housing part is included in the irradiation region.

APPENDIX 6

The mammography apparatus according to any one of Appendixes 1 to 5, in which the first magnetic object is a magnetized object, and the second magnetic object is a magnet.

APPENDIX 7

The mammography apparatus according to any one of Appendixes 1 to 6,
in which the imaging table includes a third magnetic object at a predetermined second position on the placement surface,
the protective cover further includes a fourth magnetic object which is attracted to the third magnetic object by a magnetic force, and
the protective cover is configured to be magnetically attached to the predetermined second position of the imaging table by the third magnetic object and the fourth magnetic object.

APPENDIX 8

The mammography apparatus according to Appendix 7,
in which the first magnetic object and the fourth magnetic object have different forms.

APPENDIX 9

The mammography apparatus according to Appendix 7 or 8,
in which the protective cover includes a plurality of the first magnetic objects disposed at equal intervals and a plurality of the fourth magnetic objects disposed at equal intervals, and
an interval between the plurality of the first magnetic objects is different from an interval between the plurality of the fourth magnetic objects.

APPENDIX 10

The mammography apparatus according to any one of Appendixes 7 to 9, in which the third magnetic object is a magnetized object, and the fourth magnetic object is a magnet.

APPENDIX 11

The mammography apparatus according to Appendix 1, further comprising:

an irradiation unit that irradiates the placement surface with radiation; and a controller that controls the irradiation unit, in which the controller controls the irradiation unit such that at least a part of the housing part is irradiated with the radiation and at least a part of the breast is not irradiated with the radiation.

APPENDIX 12

The mammography apparatus according to Appendix 11, in which the controller controls the irradiation unit such that at least a part of the breast and the predetermined first position are not irradiated with the radiation.

APPENDIX 13

A mammography apparatus comprising:

an imaging table that has a placement surface on which a breast is placed and includes a first magnetic object disposed at a predetermined first position on the placement surface; and a sample tray that includes a second magnetic object and a housing part of a sample and is placed on the placement surface, the second magnetic object being attracted to the first magnetic object by a magnetic force, in which the sample tray is configured to be magnetically attached to the predetermined first position of the imaging table by the first magnetic object and the second magnetic object.

APPENDIX 14

A sample imaging assistance set comprising:

a protective cover that includes a first magnetic object and is mounted on a placement surface of a mammography apparatus on which a breast is placed; and a sample tray that includes a second magnetic object and a housing part of a sample, the second magnetic object being attracted to the first magnetic object by a magnetic force.

What is claimed is:

1. A mammography apparatus comprising:

an imaging table that has a placement surface on which a breast is placed;

a protective cover that includes a first magnetic object at a predetermined first position and is mounted on the placement surface; and a sample tray that includes a second magnetic object and a housing part of a sample and is placed on the placement surface via the protective cover, the second magnetic object being attracted to the first magnetic object by a magnetic force, wherein the sample tray is configured to be magnetically attached to the predetermined first position of the protective cover by the first magnetic object and the second magnetic object.

2. The mammography apparatus according to claim 1, wherein:

the protective cover includes the first magnetic objects at each of a plurality of the predetermined first positions disposed at intervals, and the sample tray includes a plurality of the second magnetic objects disposed to correspond to a disposition of the plurality of predetermined first positions.

3. The mammography apparatus according to claim 1, wherein:

the protective cover includes a tray placement region which includes the predetermined first position and on which the sample tray is placed in a state where the protective cover is mounted on the placement surface, and the tray placement region is a region on an end part side from a center in a width direction orthogonal to a depth direction from a chest wall toward a nipple of the breast placed on the protective cover.

4. The mammography apparatus according to claim 1, wherein:

the protective cover includes a tray placement region which includes the predetermined first position and on which the sample tray is placed in a state where the protective cover is mounted on the placement surface, and the tray placement region is a region on a chest wall side from a center in a depth direction from a chest wall toward a nipple of the breast placed on the protective cover.

5. The mammography apparatus according to claim 1, wherein:

the protective cover includes, in a state where the protective cover is mounted on the placement surface:

an irradiation region which is irradiated with radiation;

a non-irradiation region which is not irradiated with radiation; and a tray placement region on which the sample tray is placed and which includes the predetermined first position, and in the tray placement region, at least the predetermined first position is included in the non-irradiation region, and a remaining region including the housing part is included in the irradiation region.

6. The mammography apparatus according to claim 1, wherein:

the first magnetic object is a magnetized object, and the second magnetic object is a magnet.

7. The mammography apparatus according to claim 1, wherein:

the imaging table includes a third magnetic object at a predetermined second position on the placement surface, the protective cover further includes a fourth magnetic object which is attracted to the third magnetic object by a magnetic force, and the protective cover is configured to be magnetically attached to the predetermined second position of the imaging table by the third magnetic object and the fourth magnetic object.

8. The mammography apparatus according to claim 7, wherein the first magnetic object and the fourth magnetic object have different forms.

9. The mammography apparatus according to claim 7, wherein:

the protective cover includes a plurality of the first magnetic objects disposed at equal intervals and a plurality of the fourth magnetic objects disposed at equal intervals, and an interval between the plurality of the first magnetic objects is different from an interval between the plurality of the fourth magnetic objects.

10. The mammography apparatus according to claim 7, wherein:

the third magnetic object is a magnetized object, and the fourth magnetic object is a magnet.

11. The mammography apparatus according to claim 1, further comprising:

an irradiation unit that irradiates the placement surface with radiation; and a controller that controls the irradiation unit, wherein the controller controls the irradiation unit such that at least a part of the housing part is irradiated with the radiation and at least a part of the breast is not irradiated with the radiation.

12. The mammography apparatus according to claim 11, wherein the controller controls the irradiation unit such that at least a part of the breast and the predetermined first position are not irradiated with the radiation.

13. A mammography apparatus comprising:

an imaging table that has a placement surface on which a breast is placed and includes a first magnetic object disposed at a predetermined first position on the placement surface; and a sample tray that includes a second magnetic object and a housing part of a sample and is placed on the placement surface, the second magnetic object being attracted to the first magnetic object by a magnetic force, wherein the sample tray is configured to be magnetically attached to the predetermined first position of the imaging table by the first magnetic object and the second magnetic object.

14. A sample imaging assistance set comprising:

a protective cover that includes a first magnetic object and is mounted on a placement surface of a mammography apparatus on which a breast is placed; and a sample tray that includes a second magnetic object and a housing part of a sample, the second magnetic object being attracted to the first magnetic object by a magnetic force.

\* \* \* \* \*